United States Patent [19]

Jessel, Jr. et al.

[11] Plant 4,778

[45] Oct. 20, 1981

[54] GERANIUM PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 175,751

[22] Filed: Aug. 5, 1980

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A new and distinct geranium plant and characterized by orange-red flower color, medium plant height, medium internode length, semi-double flower form, semi-spreading branching pattern, mid-season spring-pot flowering response, prolific outdoor summer flowering traits, good foliage durability, and good flower durability under outdoor summer conditions.

1 Drawing Figure

The present invention comprises a new and distinct cultivar of geranium, a hybrid of the genus Pelargonium, L'Her., hereinafter referred to by the cultivar name Songster.

Songster is a product of a planned breeding program which had the objective of creating new geranium cultivars with red or orange-red flower color, mid-season spring pot flowering period, medium plant height, semi-spreading branching pattern, and durable flowers and foliage characteristics under outdoor summer flowering conditions.

Songster was originated from a hybridization made in a controlled breeding program in Barberton, Ohio in 1974. The female parent was a scarlet red semi-double seedling (unnamed, #71104011) originated by the present inventors from a hybridization of two unnamed seedlings. The male parent of Songster was an orange-red semi-double seedling (unnamed, #69175001) originated by the present inventors from a hybridization of two unnamed seedlings.

Songster was discovered and selected as one flowering plant within the progeny of the stated cross by Walter H. Jessel, Jr. and William E. Duffett on June 10, 1975 in a controlled environment in Barberton, Ohio.

The first act of asexual reproduction of Songster was accomplished when vegetative cuttings were taken from the initial selection in June, 1975 in a controlled environment by a technician working under formulations established and supervised by Walter H. Jessel, Jr. and William E. Duffett. Horticultural examination of selected units has demonstrated that the combination of characteristics as herein disclosed for Songster are firmly fixed and are retained through successive generations of asexual reproduction.

Songster has not been observed under all possible environmental conditions. The phenotype may vary significantly with variations in environment such as temperature, light intensity, and day length. The following observations, measurements, and comparisons describe plants grown in Barberton, Ohio and in Salinas, Calif. under environmental conditions which approximate those generally used in commercial practice.

The following traits have been repeatedly observed and are determined to be basic characteristics of Songster which in combination distinguish this geranium as a new and distinct cultivar:

(1) Orange-red flower color, (2) Medium plant height, (3) Medium internode length, (4) Semi-double flower form, (5) Semi-spreading branching pattern, (6) Mid-season spring-pot flowering response, (7) Prolific outdoor summer flowering traits, (8) Good foliage durability under outdoor summer conditions, (9) Good flower durability under outdoor summer conditions, and

(10) Dark green foliage color with pronounced dark zonation.

Of the several commercially available geraniums known to the present inventors, the most similar in comparison to Songster are Orange Ricard (unpatented) and Yours Truly (unpatented). Reference is made to Chart A which compares certain characteristics of Songster with those same characteristics of Orange Ricard and Yours Truly. General comparisons are as follows:

(1) In comparison to Orange Ricard, Songster has more red flower color, smaller average corolla diameter, and shorter plant height. The flowering response period, branching pattern and internode length of Songster are similar to those same characteristics of Orange Ricard.

(2) In comparison to Yours Truly, Songster has smaller average corolla diameter. The corolla color, flowering response period, internode length, branching pattern and height of Songster are similar to those same characteristics of Yours Truly.

The accompanying photographic drawings show typical flower and foliage characteristics of Songster, with colors being as true as possible with illustrations of this type.

In the following description, color references are made to A Limit Color Cascade, by the Munsell Company, 1972 edition. Color values were determined between 11:30 A.M. and 12:00 Noon on Mar. 31, 1980 under 125 foot-candle light intensity at Salinas, Calif.

Botanical classification: A hybrid of the genus Pelargonium, L'Her. cv Songster

I. INFLORESCENCE

A. Umbel:
*Average diameter.*—13 cm.
*Average depth.*—75 to 80 mm.
*Peduncle length.*—23 mm.
*Pedicel length.*—From 15 to 20 cm. averaging 17 cm.

B. Corolla:
*Average diameter.*—40 to 45 mm.
*Form.*—Semi-double; rotate.
*Color (general tonality from a distance of three meters).*—34-12.
*Color (abaxial).*—Approximately 35-12 to 36-12.
*Color (adaxial).*—36-9.

C. Bud:
*Shape.*—Conodial.
*Color (adaxial).*—35-12.

D. Reproductive organs:
*Androecium.*—Monodelphous, dorsifixed, pentadynamous stamen, scant to moderate pollen.
*Gynoecium.*—5-lobed, linear stigma; pubescent, 5-loculed carpel.

E. Spring flowering response period: Mid-season, 70% of plants with at least 1 flower open 8 weeks after stick of unrooted cutting.

F. Outdoor flower production: Medium; flower count in 1976 averaged between 1.8 and 3.2 flowers per plant for June through September observation period.

G. Durability:
*Shatter resistance.*—Good.
*Tolerance of botrytis.*—Good.

II. PLANT

A. Foliage:
*Form.*—Reni-form.
*Margin.*—Undulate; crenate.
*Color (abaxial).*—21-14 to 21-15.
*Color (adaxial).*—21-14 overlaid with white.
*Color (zonation).*—Approximately 32-16 but more intense.
*Tolerance of botrytis.*—Good.

B. General appearance and form:
*Internode length.*—Medium.
*Branching pattern.*—Semi-spreading, produces mound type growth.
*Height.*—Medium.

CHART A

COMPARISON OF SONGSTER, ORANGE RICARD AND YOURS TRULY

| CULTIVAR | COROLLA COLOR | AVERAGE COROLLA DIAMETER | SPRING FLOWERING RESPONSE |
|---|---|---|---|
| SONGSTER | Orange Red | 40–45 mm. | Mid-season |
| ORANGE RICARD | Orange | 50 mm. | Mid-season |
| YOURS TRULY | Orange red | 50 mm. | Mid-season |

| CULTIVAR | BRANCHING HABIT | INTERNODE LENGTH | PLANT HEIGHT |
|---|---|---|---|
| SONGSTER | Semi-spreading | Medium | Medium |
| ORANGE RICARD | Semi-spreading | Medium | Tall |
| YOURS TRULY | Semi-spreading | Medium | Medium |

COMPARISONS MADE BETWEEN NON-PINCHED PLANTS GROWN IN SALINAS, CALIFORNIA AND IN BARBERTON, OHIO.

We claim:

1. A new and distinct geranium plant, a hybrid of the genus Pelargonium, L'Her., to be known by the cultivar name Songster, as described and illustrated, and particularly characterized by the combination of characteristics of orange-red flower color; medium plant height; medium internode length; semi-double flower form; semi-spreading branching pattern; mid-season spring-pot flowering response; prolific outdoor summer flowering traits; good foliage durability; good flower durability; and dark green foliage color with pronounced dark zonation.

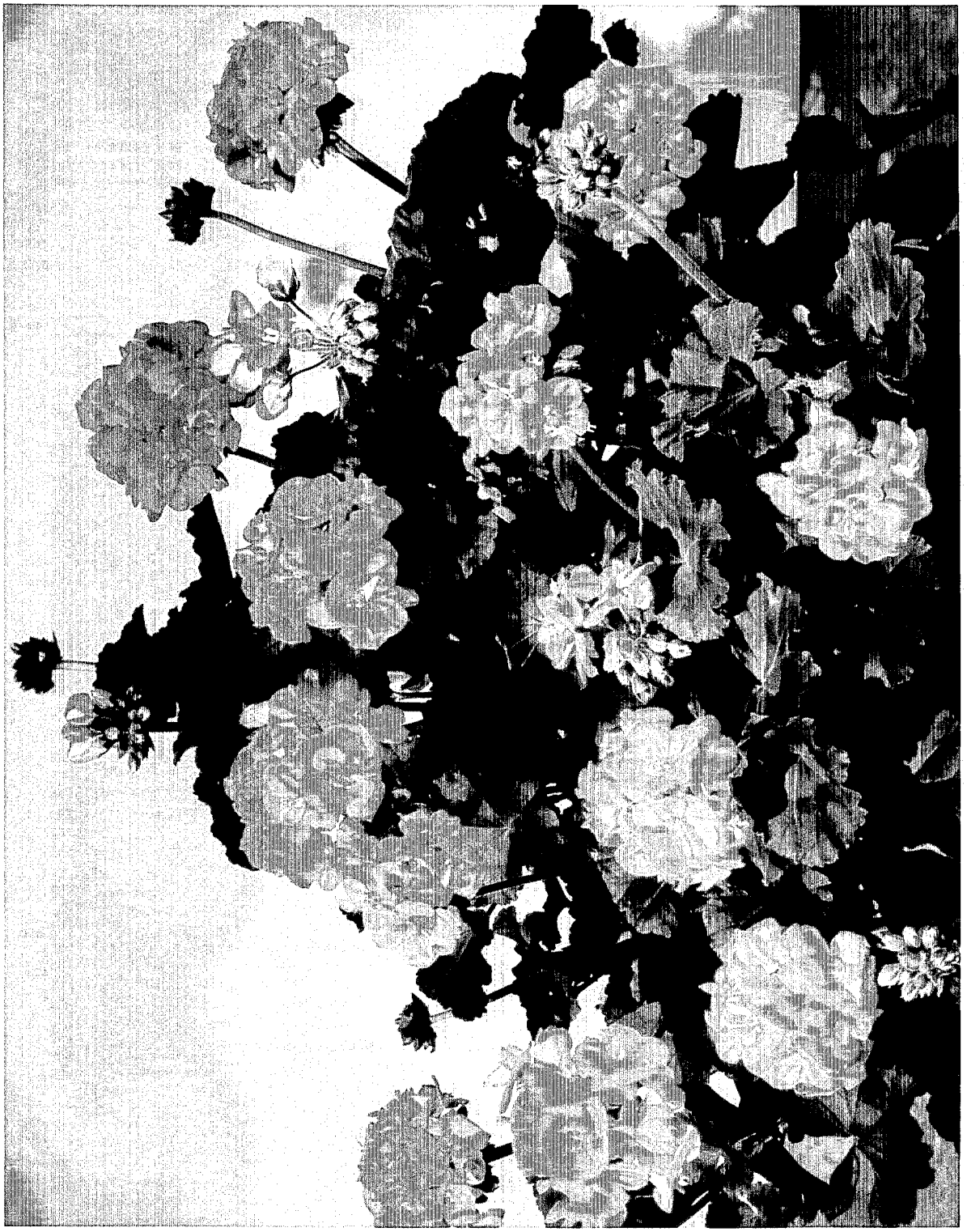

* * * * *